United States Patent [19]
Valenzuela

[11] Patent Number: 5,098,704
[45] Date of Patent: Mar. 24, 1992

[54] HEPATITIS SURFACE ANTIGEN PARTICLE VACCINE

[75] Inventor: Pablo D. T. Valenzuela, San Francisco, Calif.

[73] Assignee: Chiron Corporation, Emeryville, Calif.

[21] Appl. No.: 266,795

[22] Filed: Nov. 3, 1988

Related U.S. Application Data

[63] Continuation of Ser. No. 621,756, Jun. 18, 1984, abandoned.

[51] Int. Cl.$^5$ .............................................. A61K 39/29
[52] U.S. Cl. ........................................ 424/89; 424/88; 424/85.8; 424/86
[58] Field of Search ............... 530/350, 363, 402, 403, 530/405, 409, 810, 820; 435/68; 424/88, 89, 85, 86

[56] References Cited

U.S. PATENT DOCUMENTS

| | | | |
|---|---|---|---|
| 4,741,901 | 5/1988 | Levinson et al. | 424/89 |
| 4,769,238 | 9/1988 | Ratter et al. | 424/89 |
| 4,778,784 | 10/1988 | Dreasman et al. | 530/326 |
| 4,816,564 | 3/1989 | Ellis et al. | 530/350 |
| 4,818,527 | 4/1989 | Thornton et al. | 530/806 |
| 4,847,080 | 7/1989 | Neurath et al. | 424/89 |
| 4,935,235 | 6/1990 | Ratter et al. | 424/89 |

OTHER PUBLICATIONS

Valenzuela, P., et al., *Nature* (1979) 280: 815–819.
Valenzuela, P., et al., *Animal Virus Genetics* (1980) pp. 57–70.
Thung, S. N., et al., *Liver* (1981) 1: 75–80.
Valenzuela, P., et al., *Nature* (1982) 298: 347–350.
Stibbe, W. et al., *J. of Virol.* (1983) 46(2): 626–628.
Machida, A., et al., *Gastroenterology* (1983) 85: 268–274.
Neurath, A. R. et al., *Science* (1984) 224: 392–395.
Machida, A., et al., *Gastroenterology* (1984) 86: 910–918.
Michel, M. L., et al., *Int. Symp. on Viral Hepatitis*, 1984.

*Primary Examiner*—Garnette D. Draper
*Attorney, Agent, or Firm*—Morrison & Foerster

[57] ABSTRACT

Vaccines are provided produced by hybrid DNA technology for Hepatitis B virus comprising Hepatitis B surface antigen particles containing a human polyalbumin binding site receptor. Constructs are provided for expression of the vaccine protein, which upon transformation in an appropriate host results in the production of particles useful as vaccines.

6 Claims, 1 Drawing Sheet

HEPATITIS SURFACE ANTIGEN PARTICLE VACCINE

This application is a continuation of application Ser. No. 621,756, filed June 18, 1984 now abandoned.

BACKGROUND OF THE INVENTION

1. Field of the Invention

The precise mechanisms that control the entry of viruses into the cytoplasm or nuclei are poorly understood. There is evidence that different viruses bind to unique receptor molecules on the plasma membrane of most cells. These receptors determine, at least in part, the host and tissue specificities of certain virus infections. It has been postulated that Hepatitis B virus (HBV) has binding sites for polymerized human serum albumin serves as an agent for the specific introduction of HBV into human hepatocytes.

It would therefore be desirable to provide vaccines which involve the determinant sites essential to the infectious properties of the virus. Furthermore, the viral proteins or particles may be used for antibody production for use in diagnostic assays and treatment.

2. Description of the Prior Art

Machida et al., *Gastroenterology* (1983) 85:268-274 has disclosed evidence suggesting the existence of polyalbumin receptors on Hepatitis B surface antigen (HBsAg). See also, Machida, et al., ibid. (1984) 86:910-918). The receptor was indicated as a polypeptide of 31 kilodaltons (kd), found in low amounts in serum derived HBsAg particles (Stibbe and Gerlich, *J. Virol.* (1983) 46:626-628. The entire genome of HBV has been cloned in *E. coli* and its nucleotide sequence determined (Valenzuela et al., *Nature* (1979) 280:815-819; Valenzuela et al., *Animal Virus Genetics* (1980) pp 57-70). Hepatitis B surface antigen particles have been synthesized and assembled in *S. cerevisiae*, Valenzuela et al., *Nature* (1982) 298:374-350. Binding of human serum polyalbumin to HBV in HBsAg particles has been reviewed by Thung and Gerber, *Liver* (1981) 1:75-80. Neurath, et al., *Science* (1984) 224:392-394 describes the 55 amino acids of the pre-surface (pre-S) region as containing a new dominant epitope. Michel, et al., *Int. Symp. on Viral Hepatitis,* 1984, describes the synthesis of the pre-S-sAg particle in chinese hamster ovary cells using a SV40-dihydrofolatereductase vector.

SUMMARY OF THE INVENTION

DNA constructs, their use and transformation of hosts, and expression of the HBV surface antigen joined at the N-terminus to a substantial proportion of the amino acid sequence of the pre-S protein. The resultant particles contain a new epitope (see Neurath et al., *Science* (1984) 224:392-394) as well as human polyalbumin binding sites. The particles can be used to generate antibodies that will directly interfere with the HBV infectious process.

DESCRIPTION OF THE SPECIFIC EMBODIMENTS

Figure 1:
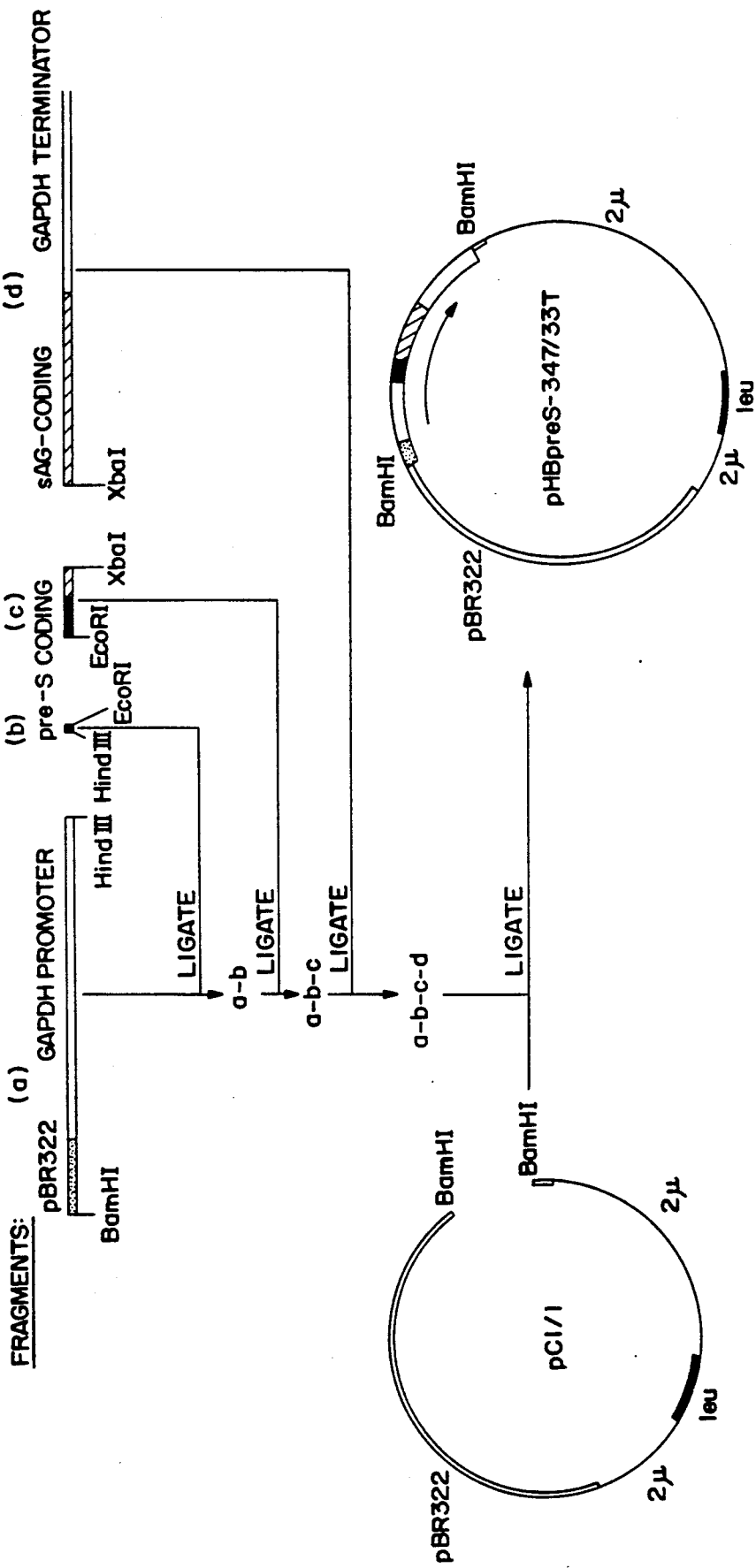
FIG. 1 is a diagrammatic view of the construction of the plasmid of pHBpreS-347/33T.

Methods and compositions are provided for producing novel vaccines to HBV, where the polypeptide includes at least a portion of the pre-S protein to provide for a human serum polyalbumin site. The protein vaccines employing the polypeptide, particularly in the form of particles, can be used by itself or in conjunction with human serum polyalbumin, as a vaccine for protecting humans against HBV. Particularly, constructs are provided for expression in yeast, where high yields of the polypeptide are obtained in particulate form, which can be used directly as vaccines, as well as serving as antigens, and as binding agents for human serum polyalbumin, where the polypeptides may be used by themselves or in combination with the polyalbumin, or the like.

Since the sequence of the complete HBsAg gene has been cloned, this gene can be obtained from a cloning vector by appropriate restriction and as necessary, employing adapters, resection or the like, to provide for the appropriate termini. Since the gene has been cloned and expressed in a vector, restriction may also include the gene or portions of the gene with appropriate transcriptional or translational regulatory signals. The HBsAg gene or fragment thereof may be joined to a polynucleotide sequence encoding for the remainder of the HBsAg gene and as appropriate, the codons encoding for at least a portion of the Hepatitis B pre-surface antigen, either by stepwise addition of oligonucleotide sequences or by ligation of a single fragment. Once the complete nucleotide sequence has been provided which includes the pre-surface antigen region joined to the surface antigen, any additional regulatory sequences may be ligated to the appropriate termini and the resulting cassette joined to other nucleotide sequences which provide for desired properties, such as replication, selection, amplification, or the like.

The constructs of this invention will for the most part have the following formula:

$$-Tr_p\text{-}Tr_I\text{-}(PHA_R\text{-}S)\text{gene-}Te_I\text{-}Te_p$$

wherein:

$Tr_p$ intends a transcriptional initiation regulatory domain, including one or more promoters, usually not more than two promoters, and as appropriate an operator, activator sites, cAMP site, capping site, TATA and CAT sites, etc;

$Tr_I$ intends translational initiation signals, such as a Shine-Dalgarno sequence, initiation codon as appropriate, etc.;

$Te_I$ intends a translational termination domain, such as stop codons, or the like;

$Te_p$ intends transcriptional termination signals, such as polyadenylation signal, terminator, etc.;

$(PHA_R\text{-}S)$gene intends a DNA sequence encoding for the HBV polyalbumin receptor site and the surface antigen (pre-S-sAg), which may include additional 5'-or 3'-coding or non-coding flanking regions, the non-coding regions being not more than about 120 bp, usually not more than about 90 bp, more usually not more than about 60 bp, where such flanking regions may serve as a signal sequence, to vary the properties of the protein, or the like.

The gene may code for any of the various serotypes, including combinations of the sub-type determinants d/y and w/r, more particularly adw. The protein coded for by the indicated gene is referred to as p31 by Machida et al., supra., and this designation will be used hereinafter to include the adw serotype, as well as the other serotypes.

The gene may be obtained in a variety of ways, either from messenger RNA or from the genome of HBV, preferably from the genome of HBV. The genome may be cleaved at a unique site, e.g., BamHI or EcoRI, and cloned in an appropriate host. One may then isolate the gene encoding for the pre-S-sAg by employing appropriate restriction endonucleases after restriction mapping the surface antigen gene region of the HBV genome. Where, for reasons of subsequent procedures, it may be desirable to cleave internal to the coding sequence or external to the coding sequence, various techniques can be employed to restore the lost codons or to remove superfluous base pairs, as appropriate.

Where the gene has been truncated, the lost base pairs may be restored by employing an adapter for linking to a flanking region providing for the necessary regulatory sequences. Where superfluous base pairs exist, these may be removed in substantial part by resection, employing an exonuclease, such as Bal31.

The cassette construction described above can be prepared and then inserted into an appropriate vector for introduction into a compatible host, such as a unicellular microorganism, including prokaryotes and eukaryotes, e.g., *E. coli, B. subtilis,* yeast, such as *S. cerevisiae, S. carlsbergenesis, S. pombe,* etc.; mammalian cells, e.g., 3T3, HeLa, Vero, MOLT-3, etc. The vectors may be derived from plasmids or viruses, there being a variety of replication systems having been employed including ColE1, as pBR322, 2 μm, as YEp6, R-5, as pRK290, Simian virus 40, as pSV40, bovine papilloma, as pBPV. Cos cells may be employed, where the T antigen binding site is provided on the vector. Also, for yeast, the combination of CEN3 and ARS1 may be employed for extrachromosomal maintenance. Alternatively, systems may be employed which allow for integration, such as transposons, Ti plasmids, Ri plasmids, and fragments thereof, as well as sequences of DNA homologous with the host genome.

Included on the vector will usually be a gene which allows for selection, due to biocidal resistance, e.g., antibiotic resistance, toxin resistance, heavy metal resistance, or the like; affording prototrophy to an auxotrophic host, e.g., leu⁻, his⁻, etc.; or affording amplification under stress, such as the genes for dihydrofolate reductase and metallothioneins, e.g., copper chelatin. The vector may be a low or high copy number replication system with low copy number being in the range from about 1-5 and high copy number being in the range of greater than 5 to 100 or more.

The various fragments may be joined by any convenient means, the particular protocol depending upon the available restriction sites, ease of providing adapters, available fragments, choice of host, and the like.

Of particular interest is a construction employed in yeast, utilizing a high performance promoter, the glyceraldehyde-3-phosphate dehydrogenase (GAPDH) promoter region in conjunction with the GAPDH terminator region. The GAPDH promoter region will have at least 200 base pairs and not more than 1500 base pairs, more usually about 300 to about 1100 base pairs, while the GAPDH terminator region will have at least 300 bp and not more than 1500 bp, more usually from about 300 to 1200 bp. The fragment may extend to the initiator codon of the GAPDH gene, usually not including the initiator codon and will generally be not more than 15 (−15), more usually not more than about 10 bases (−10) upstream from the initiation codon. The terminator region may include the stop codons of the GAPDH gene and will usually begin not more than about 30 bp from the GAPDH stop codons, more usually not more than about 20 bp from the GAPDH stop codons. The construction described above is particularly useful in combination with the 2 μm plasmid replication system, desirably forming a plasmid of less than about 20 kb, more desirably less than about 16 kb.

The expression constructs comprising the vector and the expression cassette may be introduced into a compatible host by any convenient technique, such as transformation, e.g., polyethylene glycol precipitation, conjugation, transfection, transduction, or the like. The recipient cells may then be grown in an appropriate nutrient medium to a desired density, the cells harvested, a lysate prepared by any convenient means, e.g., agitation with glass beads, and the desired protein harvested. It is found that the p31 protein assembles, so as to form particles of density similar to the known HBsAg particles. Particles can be prepared which are at least 10 mole %, usually at least 30 mole % more usually 50 to 80 mole % of the p31 protein prepared by recombinant technology.

The p31 particles are capable of binding to human serum polyalbumin. The particles of the p31 polypeptide are provided in high yield and can be readily isolated in pure form by conventional techniques. Conveniently, the particles may be isolated by affinity chromatography employing a column containing polymerized human serum albumin. Alternatively, separations can be employed using density gradients, gel filtrations, and the like. The techniques may be used individually or in combination.

The p31 protein, by itself or assembled as particles, may be used in a variety of ways. Of particular interest is the use of the p31 protein or particle, by itself or in combination with polymerized human serum albumin, individually or as particles, as a vaccine. Any of the conventional methods for administration of a dead virus vaccine are applicable. These include applications on a solid physiologically acceptable base or in a physiologically acceptable dispersion, parenterally, by injection, or the like. The dosage of the vaccine will depend on the route of administration and will vary according to the size of the host. Because the vaccine will have few, if any, side effects, relatively large doses may be used without injury to the host. Normally, the amount of the vaccine will be from about 1 μg to 20 mg per kilogram of host, more usually from about 5 μg to 20 μg given subcutaneously or intramuscularly, after mixing with an appropriate carrier or an adjuvant to enhance immunization with the vaccine.

Various methods of achieving adjuvant effect for the vaccine include use of agents such as aluminum hydroxide or phosphate (alum), commonly used as a 0.05 to 0.1% solution in phosphate buffered saline, admixture with synthetic polymers of sugars (Carbopol), used as a 0.25% solution mixture with bacterial cells such as *C. parvum* or endotoxins or lipopolysaccharide components of Gram-negative bacteria, emulsion in physiologically acceptable oil vehicles, such as mannide monooleate (Aracel A) or emulsion with a 20% solution of a perfluorocarbon (Fluosol-DA) used as a blood substitute.

The amount of the adjuvant which is employed will vary widely depending upon the nature of the adjuvant, generally ranging from 0.1 to 100 times the weight of the immunogen, more usually from about 1 to 10 times.

In many instances it will be desirable to have multiple administrations of the vaccine, usually not exceeding six vaccinations, more usually not exceeding four vaccinations, and preferably one or more, usually about three vaccinations. The vaccinations will normally be at from 2 to 12 week intervals, more usually from 3 to 5 week intervals, with optional periodic boosters at intervals of 1 to 5 years. The course of the immunization may be followed by assays for antibodies for HBV.

The subject p31 proteins or particles can also be used in assays for detecting the presence of antibodies to HBV or complexes of HBV and polymerized serum albumin. In use in assays, the protein or protein complex will normally be labeled with one of a variety of labels which find use in assays. These labels have been extensively reported in the patent and technical literature, and include radionuclides, fluorescers, enzymes, enzyme substrates, particles, small molecules, and the like. Alternatively, the p31 protein or particle can be used for detection of the presence of polymerized serum albumin or removal of polymerized serum albumin from a physiological fluid, e.g., blood.

The wild type p31 protein serotypes need not be employed since one or more amino acids may be added, deleted or substituted so long as the serum albumin binding property and immunological properties are retained. Thus, at least 90, usually at least 95, more usually at least 99 number percent of the amino acids will be the correct amino acids and in the correct sequence. Usually, any changes will be at the N-terminus where from 0 to 5 amino acids may differ.

The p31 protein prepared by hybrid DNA technology may be used by itself or in combination with polymerized human serum albumin, individually or as particles, for the production of antibodies in various mammalian hosts, e.g., murine, bovine, ovine, lagomorpha, human, etc. The antibodies can then be used in immunoassays for the detection of the presence of the p31 protein or p31-polymerized albumin complex or may be administered in vivo in conventional ways to a mammalian host.

The following examples are offered by way of illustration and not by way of limitation:

EXPERIMENTAL

All DNA manipulations were done according to standard procedures. See *Molecular Cloning*, T. Maniatis et al., Cold Spring Harbor Lab., 1982. Enzymes used in cloning were obtained either from New England Biolabs or Bethesda Research Laboratories and employed according to the supplier's directions. Yeast were transformed and grown using a variety of media including selective medium (yeast nitrogen base without leucine); YEPD medium, containing 1% (w/v) yeast extract, 2% (w/v) peptone and 2% (w/v) glucose, and others as appropriate and/or detailed below. In the case of plating medium contained 2% (w/v) agar and for transformation 3% top agar.

1. Construction of preS-sAg Expression Vectors

A cassette containing the yeast glyceraldehyde-3-phosphate dehydrogenase (GAPDH) promoter region; the pre-S HBV region comprising 165 bp encoding 55 amino acids; the coding sequence for the surface antigen (sAg) gene in reading frame with pre-surface (pre-S) sequence; and the GAPDH terminator region, was prepared by ligating the following four fragments: a) a 1407 BamHI-HindIII fragment that contains the GAPDH promoter; b) a 14 bp HindIII-EcoRI adapter molecule coding for the first three amino acids of the pre-S region; c) a 250 bp EcoRI-XbaI fragment encoding a segment of the pre-S region (52 amino acids) and the first 32 amino acids of the sAg N-terminal region, and d) an approximately 1580 bp XbaI-BamHI fragment containing sAg coding region and the GAPDH terminator (FIG. 1).

These four fragments were ligated in steps as follows: 4 picomoles fragment a (GAPDH promoter) were ligated to 260 picomoles of phosphorylated fragment b (14 bp synthetic adaptor) in the presence of 10 units of T4 DNA ligase. The product (fragment a-b) was separated from an excess of adaptor molecules by preparative gel electrophoresis. Approximately 1.5 picomole of isolated fragment a-b was ligated to 1.5 picomoles of fragment c (250 bp EcoRI-XbaI pre-S and sAg N-terminal region) in the presence of 10 units of T4 DNA ligase. Approximately 1 picomole of the product (fragment a-b-c) was ligated to 1 picomole of fragment d (1580 bp XbaI-BamHI, sAg C-terminal region and GAPDH terminator) and to 0.01 picomole of BamHI-digested yeast vector pC1/1 in the presence of 5 units of T4 DNA ligase. Plasmid pC1/1 is a derivative of pJDB219, Beggs, Nature (1978) 754:104, in which the region corresponding to the bacterial plasmid pMB9 in pJDB219 has been replaced by pBR322 in pC1/1. A plasmid containing the cassette cloned in pC1/1 was isolated after transformation of *E. coli* HB101. This plasmid was named pHBpreS-347/33T (FIG. 1). The strategy followed to obtain fragments a, b, c and d is described below.

Fragment a) A 1407 bp BamHI-HindIII fragment containing 346 bp of pBR322 and a 1061 bp of the GAPDH promoter was prepared by digestion of plasmid pHBS56-GAP347/33 (50 μg) with BamHI and HindIII (10 units each). The fragment was isolated by preparative gel electrophoresis in 1% agarose. Plasmid pHBS56-GAP347/33 was prepared as follows.

A complementary DNA (cDNA) containing the yeast GAPDH coding sequences was prepared in the following manner (see copending application Serial No. 468,589, filed Feb. 22, 1983):

PolyA+ RNA was isolated from *S. cerevisiae* yeast strain A364A. Double-stranded cDNA was synthesized using AMV reverse transcriptase and *E. coli* DNA polymerase I. Poly-dC-tails were added to the double-stranded cDNA molecule using deoxynucleotide terminal transferase. Poly-dC-tailed cDNA was annealed to poly-dG-tailed pBR322 and used to transform *E. coli* HB101. 1000 transformants were screened by colony hybridization to labeled PolyA+ RNA, and a subset further examined by restriction endonuclease mapping, and DNA sequencing. Three clones containing GAPDH sequences were isolated from the pool. One clone (pcGAP-9) contained an insert of about 1200 base pairs and was used for further work.

A yeast gene library was prepared by inserting fragments obtained after partial digestion of total yeast DNA with restriction endonuclease Sau3A into lambda phage Charon 28, according to Blattner, F. R. et al., *Science*, 196, 161–169 (1977). Several fragments containing yeast GAPDH coding sequences were isolated by screening the phage library with labeled DNA from pcGAP-9. The yeast GAPDH gene of one of these clones was subcloned in pBR322 as a 2.1 kb HindIII fragment (pGAP-1). The GAPDH promoting-active fragments were isolated from these clones. A HhaI-HindIII fragment of about 350 bp containing the 3' portion of the promoter was obtained by: a) digestion of pGAP-1 with HinfI to generate an approximately 500 bp segment which includes the 3' part of the promoter and a region encoding the N-terminal amino acids of GAPDH; b) resection with Bal31 to yield a 400 bp fragment lacking the GAPDH coding region (3'-terminus 1 base upstream from the ATG initiator codon); c) addition of HindIII linkers; and d) cleavage with HhaI. A second HindIII-HhaI fragment of about 700 bp containing the 5' portion of the promoter was isolated from pGAP1, ligated to the 350 bp HhaI-HindIII fragment and treated with HindIII. The resulting 1,061 bp HindIII fragment was isolated by gel electrophoresis and cloned in HindIII digested, alkaline phosphatase treated pBR322 (pGAP-347).

A plasmid vector (pHB556-GAP347/33), for the expression of HBV surface antigen in yeast, using the GAPDH promoter fragment was constructed. Total digestion of pGAP-347 with SphI followed by partial digestion with HindIII yielded an approximately 1700 base pair SphI-HindIII fragment having about 1060 base pairs which included the GAPDH promoter and about 530 base pairs of pBR322. The 1700 base-pair SphI-HindIII GAPDH promoter fragment was ligated with the 840 base-pair HindIII-HindIII fragment (containing the HBsAg coding region, 26 bases of 5' non-coding region and 128 base pairs of 3' non-coding region, obtained from pHBS-56) and then with the 350 base-pair HindIII-SphI fragment containing the ADH-1 termination region (isolated from pHBS-56). The 2,900 base-pair SphI fragment (cassette) was isolated and cloned in pHBS-56 previously digested with SphI. The resulting plasmid (pHBS-56GAP347/33) in which the promoter, gene and termination regions were in the proper orientations was isolated.

Plasmid pHBS56 was obtained as follows: A TaqI-HpaI fragment obtained from the HBsAg coding region which included 26 bp of the pre-S region, 681 bp of the sAg region and 128 bp of the 3'-untranslated region, was ligated to EcoRI linkers and cloned at the EcoRI site in pBR322. The EcoRI linkers have the sequence GGAATTCC. The plasmid pHBS5 was thus obtained.

The HBsAg-DNA segment of pHBS5 was excised by EcoRI digestion, blunt-ended with the Klenow fragment and joined at both ends with HindIII linkers, CAAGCTTG. After digestion with HindIII, the HBsAg fragment was inserted into the HindIII site of the plasmid pADH5 which had been digested at the HindIII site intermediate the ADH1 promoter and terminator sequence. A plasmid with the HBsAg gene in the correct orientation as determined by restriction analysis was designated pHBS22. The cassette was included between two SphI restriction sites. pHBS22 was digested with SphI to obtain a fragment of about 1500 bp and inserted into SphI digested pC1/1 to provide pHBS56.

pADH5 was obtained as follows. A 1500 bp ADH1 promoter fragment terminating at position −9 (Hitzeman et al., *Nature* (1981) 293:717) and an approximately 450 bp terminator unit from nucleotides 913 to 1368 in the ADH gene nucleotide sequence were joined at a HindIII site between the fragments and cloned into the BamHI site of the vector YEp13 (Broach and Hicks, *Gene* (1979) 8:121) to provide pADH5.

Fragment b) A 14 bp HindIII-EcoRI adapter molecule coding for the first three amino acids of the pre-S region (met-glu-trp) and including the five additional bases for the restriction sites was obtained by chemical synthesis

```
5'-AGCTTATGCAGTGG-3'
3'-ATACGTCACCTTAA-5'
```

Fragment c) A 250 bp EcoRI-XbaI fragment encoding a segment of the Hepatitis B pre-surface (pre-S) antigen region (52 amino acids) and the first 32 amino acids of the surface antigen (sAg) N-terminal region was obtained by digestion of plasmid pHBV-3200 (50 µg) (Valenzuela et al., *Nature* (1979) 280:815–819) with the enzymes EcoRI and XbaI (10 units each) and isolated by preparative gel electrophoresis in 6% polyacrylamide.

Fragment d) An approximately 1580 bp XbaI-BamHI fragment containing about 680 bp coding for the remaining C-terminal region of the HBsAg protein (194 amino acids) and 3' HBsAg non-coding region and approximately 900 bp corresponding to the GAPDH terminator region. This fragment was obtained by digestion of the plasmid pHBS-GAP347/33T (50 µg) with XbaI and BamHI (10 units each) and the resulting 1580 bp fragment isolated by preparative gel electrophoresis.

pHBS-GAP347/33T contains the sAg coding region inserted between the GAPDH promoter and GAPDH terminator, with the whole expression cassette flanked by BamHI restriction sites. The GAPDH promoter and part of the sAg coding sequence was obtained from pHBS56-GAP347/33 (a plasmid that contains the sAg coding region, GAPDH promoter and ADH terminator in an SphI fragment described previously). The GAPDH terminator and the rest of the sAg coding sequence was obtained from pGAP2'-sAg5-Δ.

pHBS56-GAP347/33 was digested with SphI. Recessed ends were filled in with Klenow and BamHI linkers were ligated, followed by BamHI digestion. The DNA was digested with XbaI and a 1.63 kb BamHI-XbaI fragment containing the GAPDH promoter and sAg coding region was isolated by gel electrophoresis. pGAP2'-sAg5-Δ was digested with BamHI and XbaI. A 1.5 kb fragment containing the GAP terminator and sAg coding region was isolated by gel electrophoresis. Both fragments were ligated to a BamHI digested pC1/1 vector. The resulting plasmid is pHBS-GAP347/33T.

pGAP2'-sAg5-Δ is a plasmid derived from pGAP2'-sAg5 in which part of the 3' non-coding region of the HBS gene and the coding region of GAPDH gene have been deleted. For this construction, two fragments were prepared. The first contains the vector with the GAP promoter. This fragment was obtained by digestion of pGAP2'-sAg5 with NcoI, followed by a partial digestion with SalI. The NcoI-SalI vector band (approximately 7 kb) was purified by gel electrophoresis. The second fragment containing the sAg coding region with 128 base pairs of 3' untranslated region was obtained by NcoI-HpaI digestion of pGAP2'-sAg5. The 0.8 kb fragment was isolated by gel purification. Both fragments were ligated through their NcoI sticky ends, the recessed ends were filled in with Klenow and the resulting blunt ends ligated to yield pGAP2'-sAg5-Δ.

pGAP2'-sAg5 was constructed by cloning a fragment containing the HBsAg coding and 3' non-coding regions purified from pHBS5-3 Hae2-1 into pGAP-2'. To prepare the fragment, pHBS5-3 Hae2-1 was linearized by PstI digestion and partially digested with NcoI. A fragment of 1.9 kb containing part of pBR322 sequences, HBsAg coding and 3' sequences was purified by gel electrophoresis. This fragment was subsequently digested with EcoRI and a 1.2 kb NcoI-EcoRI fragment containing HBsAg coding and 3' sequences was purified by gel electrophoresis. pGAP-2' was linearized with XbaI and treated with Bal31 to remove approximately 100 base pairs. The plasmid was subsequently digested with NcoI and a fragment of approximately 8 kb was purified by gel electrophoresis. The NcoI ends of vector and fragment were ligated. The recessed ends were filled in with Klenow and the blunt ends were ligated. The resulting plasmid is pGAP2'-sAg5.

pHBS5-3 Hae2-1 is a derivative of pHBS5-3 (a plasmid that contains the HBsAg coding region and part of 3' flanking sequences), which contains more 3' non-coding sequences. To prepare a fragment containing a longer HBS non-coding region, the HBV genome (3.2 kb) was excised from pHB-3200 (Valenzuela et al., 1979, Nature, 280:815–819) by restriction digestion with EcoRI. The 3.2 kb fragment was purified by gel electrophoresis and was recircularized by ligation of the EcoRI sticky ends. This closed HBV genome was digested with HaeII, which cuts in the 3' non-coding region. Recessed ends were filled in with Klenow and HindIII linkers were ligated. The DNA was cut with HindIII and subsequently with XbaI, which has a single site in the HBS coding region. A 1.2 kb XbaI-HindIII fragment containing 586 base pairs of the coding sequence of HBV and 607 base pairs of the 3' non-coding region was isolated by gel electrophoresis. This fragment was cloned into pHBS5-3 previously cut with XbaI and HindIII and treated with alkaline phosphatase, to yield pHBS5-3 Hae2-1.

Plasmid pHBS5-3 was constructed as follows: A TaqI-HpaI fragment obtained from the HBsAg coding region which included 26 bp of the pre-sAg region, 681 bp of the sAg region and 128 bp of the 3'-untranslated region, was linked with EcoRI linkers and cloned at the EcoRI site in pBR322. The EcoRI linkers have the sequence GGAATTCC. The plasmid pHBS5 was thus obtained.

After digesting pHBS5 with EcoRI, the digest was resected with Bal31 and religated with EcoRI linkers (GGAATTCC). After digestion with EcoRI the material of about 800 bp was isolated from a polyacrylamide gel. This isolate was then recloned into pBR322 which had been digested with EcoRI and treated with alkaline phosphatase. Where the resection was to the sequence CATGG, which included the methionine codon, the EcoRI linker created an NcoI site. The plasmids were screened for the presence of an NcoI site and one of the plasmids chosen for further manipulation. This plasmid was designated pHBS5-3.

pGAP-2 is a pBR322 derived vector which contains a BamHI insert that has the GAP coding sequence, 3' and 5' flanking regions. There are two XbaI sites in this plasmid: one in the coding region and one in the 3' flanking sequences. pGAP-2' is a derivative of pGAP-2 in which the XbaI site present in the 3' flanking region has been eliminated. For this purpose, 50 µg of pGAP-2 were partially digested with XbaI, treated with Bal31 to remove 25 base pairs per end and ligated. The plasmids were used to transform HB101 and the transformants were selected for loss of the XbaI site in the 3' flanking region.

2. Transformation of Yeast Strain 2150-2-3 with pHBpreS-347/33T and synthesis of HBsAg particles containing protein monomers of 31,000 daltons The plasmid pHBpreS-347/33T (1.0 µg) was used to transform yeast S. carlsbergenesis strain 2150-2-3 (MATa, ade1, leu204, cir°) which is obtained from the collection of Dr. Leland Hartwell at the University of Washington. Yeast S. carlsbergensis transformed with pHBpreS-347/33T was deposited with the American Type Culture Collection under ATCC accession no. 20716 on June 14, 1984. Availability of this strain following the issue date of this patent is guaranteed for thirty years from the date of deposit. Plasmid pHBS-GAP347/33T, which contains the region coding for sAg fused to the GAPDH promoter and terminator, was used as a control in these experiments. Transformation was performed as described by Hinnen, et al., Proc. Natl. Acad. Sci. (1978) 75:1929–1933.

One hundred ml cultures of strain 2150-2-3 containing plasmid pHBpreS-347/33T were grown to optimum density at 650 nm of 3 in leucine minus medium. Cell-free lysates were prepared by agitation with glass beads and removal of cell debris by centrifugation. HBsAg was measured by the Abbott Ausria II ® immunoassay and protein concentration was determined by the Coomassie blue binding method. The results are shown in Table I.

TABLE I

| Exp # | sAg (µ/ml) | Protein (mg/ml) | Specific Activity (µg sAg/mg protein) |
|---|---|---|---|
| (a) From pHBS-GAP347/33T | | | |
| 1 | 17.1 | 25.5 | 0.67 |
| 2 | 17.1 | 30.5 | 0.56 |
| (b) From pHBpreS-347/33T | | | |
| 1 | 31.6 | 28 | 1.13 |
| 2 | 48 | 26.3 | 1.8 |

They indicate that immunoreactive HBsAg material is synthesized from pHBpreS-347/33T in yields similar or larger than those obtained from pHBS-GAP347/33T. Experiments using CsCl and sucrose gradient sedimentation indicate that the HBsAg containing 55 amino acids of the pre-S region is assembled into particles of density similar to the known HBsAg particles.

The pre-S containing particles were purified by immuno-affinity chromatography using a monoclonal antibody against sAg. The purified particles were analyzed by protein gel electrophoresis. Results showed that the monomer of the pre-S containing particle has a molecular weight of approximately 31,000 as expected for a protein of 281 amino acids.

The ability of the pre-S-containing particles to bind human polyalbumin was investigated by a specific ELISA procedure. Polystyrene beads were coated with human polyalbumin, incubated with dilutions of the yeast cell lysates prepared as described above in 50 mM sodium phosphate (pH 7.0) and 1% BSA, incubated at 42° C. for 2 hrs, washed with H$_2$O, incubated with Abbott guinea pig anti HBsAg-peroxidase antibodies for 1 hr at 42°, washed and read at 492 nm after adding ortho-phenylenediamine reagent.

TABLE II

| | Polyalbumin Binding | |
|---|---|---|
| | Dilution | |
| Yeast Strain | 1:200 (OD$_{492}$) | 1:500 (OD$_{492}$) |
| Cl/1 Control | 0.034 | 0.018 |
| sAg pHBS-GAP347/33T | 0.110 | 0.031 |
| sAG pHBpreS-347/33T | 1.36 | 0.69 |

As is shown in Table II, the results clearly indicate that the HBsAg particles containing the 55 amino acids of the pre-S region are able to efficiently bind human polyalbumin in contrast to HBsAg particles which do not contain this region.

Although the foregoing invention has been described in some detail by way of illustration and example for purposes of clarity of understanding, it will be obvious that certain changes and modifications may be practiced within the scope of the appended claims.

What is claimed is:

1. A Hepatitis B pre-S-sAg particle comprising p31 protein prepared by recombinant DNA technology.
2. The particle of claim 1, wherein said particle is expressed in yeast.
3. The particle of claim 1, wherein said particle is bound to human serum albumin.
4. A Hepatitis B pre-S-sAg particle vaccine, comprising an immunogenic amount of p31 produced by recombinant technology, a pharmaceutically acceptable carrier, and an immunologic adjuvant.
5. A vaccine according to claim 4, wherein said particle is bound to wherein said carrier comprises human serum albumin.
6. Antibodies that are immunoreactive with the Hepatitis B pre-S-sAg particle of claim 1.

* * * * *